United States Patent
Lee et al.

(10) Patent No.: US 9,687,301 B2
(45) Date of Patent: Jun. 27, 2017

(54) SURGICAL ROBOT SYSTEM AND CONTROL METHOD THEREOF

(71) Applicant: SAMSUNG ELECTRONICS CO., LTD., Suwon-si, Gyeonggi-do (KR)

(72) Inventors: Min Hyung Lee, Anyang-si (KR); Young Bo Shim, Seoul (KR); Byung June Choi, Gunpo-si (KR); Young Do Kwon, Yongin-si (KR); Kyung Shik Roh, Seongnam-si (KR)

(73) Assignee: Samsung Elecronics Co., Ltd., Gyeonggi-do (KR)

( * ) Notice: Subject to any disclaimer, the term of this patent is extended or adjusted under 35 U.S.C. 154(b) by 126 days.

(21) Appl. No.: 13/943,962

(22) Filed: Jul. 17, 2013

(65) Prior Publication Data

US 2014/0046128 A1 Feb. 13, 2014

(30) Foreign Application Priority Data

Aug. 7, 2012 (KR) ........................ 10-2012-0086486

(51) Int. Cl.
| | | |
|---|---|---|
| A61B 19/00 | (2006.01) | |
| A61B 1/00 | (2006.01) | |
| A61B 1/04 | (2006.01) | |
| A61B 17/04 | (2006.01) | |
| A61B 5/055 | (2006.01) | |
| A61B 6/03 | (2006.01) | |
| A61B 17/062 | (2006.01) | |
| A61B 34/30 | (2016.01) | |
| A61B 34/37 | (2016.01) | |

(Continued)

(52) U.S. Cl.
CPC ...... *A61B 19/2203* (2013.01); *A61B 1/00009* (2013.01); *A61B 1/00149* (2013.01);
(Continued)

(58) Field of Classification Search
CPC ................ A61B 19/2203; A61B 19/56; A61B 2019/2223; A61B 2019/223;
(Continued)

(56) References Cited

U.S. PATENT DOCUMENTS 5,582,576 A * 12/1996 Hori .................... A61B 1/00096
600/118

(Continued)

FOREIGN PATENT DOCUMENTS

| JP | 2002-239960 | 8/2002 |
|---|---|---|
| KR | 10-0956762 | 5/2010 |

(Continued)

OTHER PUBLICATIONS

Minhyung Lee et al., "Neural-Network based Human Surgical Motion Intention Estimation for Surgical Robots", Samsung Best Paper Award 2012, pp. 1-5.

*Primary Examiner* — Khoi Tran
*Assistant Examiner* — Robert Nguyen
(74) *Attorney, Agent, or Firm* — Harness, Dickey & Pierce, P.L.C.

(57) ABSTRACT

A control method may be applied to a surgical robot system including a slave robot having a robot arm to which a main surgical tool and an auxiliary surgical tool are coupled, and a master robot having a master manipulator to manipulate the robot arm. The control method includes acquiring data regarding a motion of the master manipulator, predicting a basic motion to be performed by an operator based on the acquired motion data and results of learning a plurality of motions constituting a surgical task, and adjusting the auxiliary surgical tool so as to correspond to the operator basic motion based on the predicted basic motion. The control method allows an operator to perform surgery more comfortably and to move or fix all required surgical tools to or at an optimized surgical position.

14 Claims, 17 Drawing Sheets

(51) Int. Cl.
*A61B 5/00* (2006.01)
*A61B 5/11* (2006.01)

(52) U.S. Cl.
CPC ............... *A61B 1/04* (2013.01); *A61B 6/032* (2013.01); *A61B 17/0469* (2013.01); *A61B 17/062* (2013.01); *A61B 34/30* (2016.02); *A61B 34/37* (2016.02); *A61B 5/055* (2013.01); *A61B 5/11* (2013.01); *A61B 5/1124* (2013.01); *A61B 5/7264* (2013.01); *A61B 5/742* (2013.01)

(58) Field of Classification Search
CPC ... A61B 1/00149; A61B 1/00009; A61B 1/04; A61B 17/0469; A61B 17/062; A61B 34/30; A61B 34/37; A61B 5/055; A61B 5/11; A61B 5/1124; A61B 5/7264; A61B 5/742; A61B 6/032; A61N 2017/00207; B25J 9/1689; B25J 13/02
See application file for complete search history.

(56) References Cited

U.S. PATENT DOCUMENTS

| | | | | |
|---|---|---|---|---|
| 2005/0001842 | A1* | 1/2005 | Park | G06T 13/40 345/474 |
| 2011/0118752 | A1* | 5/2011 | Itkowitz | B25J 9/1689 606/130 |
| 2012/0330447 | A1* | 12/2012 | Gerlach | G01B 11/24 700/95 |
| 2013/0116706 | A1* | 5/2013 | Lee | A61B 34/30 606/130 |
| 2013/0172908 | A1* | 7/2013 | Sang | A61B 17/3403 |
| 2013/0218340 | A1* | 8/2013 | Hager | B25J 9/1671 700/257 |
| 2014/0257330 | A1* | 9/2014 | Choi | A61B 19/2203 606/130 |
| 2014/0275760 | A1* | 9/2014 | Lee | A61B 1/00045 600/102 |
| 2014/0288413 | A1* | 9/2014 | Hwang | A61B 34/37 600/424 |
| 2014/0303643 | A1* | 10/2014 | Ha | A61B 34/37 606/130 |
| 2014/0309659 | A1* | 10/2014 | Roh | A61B 19/2203 606/130 |
| 2014/0324070 | A1* | 10/2014 | Min | A61B 34/37 606/130 |
| 2014/0330077 | A1* | 11/2014 | Yoon | A61B 17/3423 600/109 |

FOREIGN PATENT DOCUMENTS

| | | |
|---|---|---|
| WO | WO 2007/056803 | 5/2007 |
| WO | WO 2010/093152 | 8/2010 |

* cited by examiner

SURGICAL ROBOT SYSTEM AND CONTROL METHOD THEREOF

CROSS-REFERENCE TO RELATED APPLICATIONS

This application claims the priority benefit of Korean Patent Application No. 10-2012-0086486, filed on Aug. 7, 2012 in the Korean Intellectual Property Office, the disclosure of which is incorporated herein by reference.

BACKGROUND

1. Field

Embodiments disclosed herein relate to a surgical robot system for use in minimally invasive surgery and a control method thereof.

2. Description of the Related Art

Minimally invasive surgery refers to surgical methods less invasive than open surgeries. A representative example of minimally invasive surgery includes laparoscopic surgery or surgery using a surgical robot. Differently from existing laparotomy using relatively large surgical incisions through a part of a human body (e.g., the abdomen), in minimally invasive surgery, after forming several small ports of 0.5 cm~1.5 cm (incisions or invasive holes) through the abdominal wall, an operator inserts a video camera and various appliances through the ports, to perform surgery while viewing images.

As compared to laparotomy, minimally invasive surgery has several advantages, such as low pain after surgery, early recovery, early restoration of ability to eat, short hospitalization, rapid return to daily life, and superior cosmetic effects owing to a small incision part. Accordingly, minimally invasive surgery has been used in gall resection, prostate cancer, and herniotomy operations, etc, and the use range thereof increasingly expands.

Generally, a surgical robot system may include a master robot that generates and transmits a manipulation signal entered by a doctor, and a slave robot that directly performs manipulation required for performing a surgical operation on a patient upon receiving the signal from the master robot. The master robot and the slave robot may be integrated with each other, or may be separately arranged in an operating room.

The slave robot may include a robot arm for surgical manipulation. A surgical instrument may be mounted to an end of the robot arm, and in turn a surgical tool may be mounted to an end of the surgical instrument.

In the conventional surgical robot system, if an operator (generally, a doctor for example) manipulates a master manipulator (e.g., a joystick) provided at the master robot, movement of the robot arm, surgical instrument, and surgical tool, i.e. movement of the slave robot, is controlled based on detected data regarding manipulation of the master manipulator.

SUMMARY

It is an aspect of the present invention to provide a surgical robot system and a control method thereof in which an intelligent surgical robot system predicts an operator motion and safely manipulates, e.g., a required auxiliary surgical tool during surgery based on the predicted motion, thereby improving safety and accuracy of surgery.

Additional aspects of the invention will be set forth in part in the description which follows and, in part, will be apparent from the description, or may be learned by practice of the invention.

In accordance with one aspect of the invention, a control method of a surgical robot system, the surgical robot system including a slave robot having a robot arm to which a main surgical tool and an auxiliary surgical tool are coupled, and a master robot having a master manipulator to manipulate the robot arm, includes: acquiring data regarding a motion of the master manipulator, predicting a basic motion to be performed by an operator based on the acquired motion data and results of learning a plurality of motions constituting a surgical task, and adjusting the auxiliary surgical tool so as to correspond to the operator basic motion based on the predicted basic motion.

The data regarding the motion of the master manipulator may include at least one of interactive force data between the master manipulator and the operator, position data of the master manipulator, and speed data of the master manipulator.

The surgical task may include one or more of suturing, passing, running, and cannulation.

The plurality of motions constituting the surgical task may include one or more of orient, push, and pull motions.

The learning of the plurality of motions constituting the surgical task may be performed via machine learning.

The machine learning may be supervised learning in which the data regarding the motion of the master manipulator acquired before surgery is an input and learning is performed in a state in which a target value for the input is known.

In accordance with another aspect of the invention, a control method of a surgical robot system, the surgical robot system including a slave robot having a robot arm to which a main surgical tool and an auxiliary surgical tool are coupled, and a master robot having a master manipulator to manipulate the robot arm, includes: acquiring data regarding a motion of the master manipulator, bio-data of an operator, and bio-data of a patient, predicting a basic motion to be performed by the operator based on the acquired motion data, bio-data of the operator, bio-data of the patient, and results of learning a plurality of motions constituting a surgical task, and adjusting the auxiliary surgical tool so as to correspond to the operator basic motion based on the predicted basic motion.

The data regarding the motion of the master manipulator may include at least one of interactive force data between the master manipulator and the operator, position data of the master manipulator, and speed data of the master manipulator.

In accordance with a further aspect of the invention, in a surgical robot system including a slave robot having a robot arm to which a main surgical tool and an auxiliary surgical tool are coupled, and a master robot to control the slave robot, the master robot includes a master manipulator to manipulate the robot arm, a motion data detector to detect data regarding a motion of the master manipulator, and a controller that predicts a basic motion to be performed by an operator based on the motion data detected via the motion data detector and results of learning a plurality of motions constituting a surgical task, and controls the auxiliary surgical tool so as to correspond to the operator basic motion based on the predicted basic motion.

The motion data detector may include at least one of a force/torque sensor that detects interactive force data between the master manipulator and the operator, a position sensor that detects a position of the master manipulator, and a speed sensor that detects a speed of the master manipulator.

The surgical task may include one or more of suturing, passing, running, and cannulation.

The plurality of motions constituting the surgical task may include one or more of orient, push, and pull motions.

The controller may include a first control signal generator that generates a first control signal to control a motion of the slave robot based on the data regarding the motion of the master manipulator acquired via the motion data detector, a learner that learns the plurality of motions constituting the surgical task based on the previously acquired data regarding the motion of the master manipulator, a predictor that predicts the operator basic motion or the surgical task based on the motion data detected via the motion data detector and the results of learning performed via the learner, a second control signal generator that generates a second control signal to control the motion of the slave robot and/or the master manipulator having a redundant DOF based on the predicted basic motion or surgical task, and an image processor that processes an image input from an endoscope that is one kind of the auxiliary surgical tool to output a picture image.

The surgical robot system may further include a storage unit that stores the results of learning the plurality of motions constituting the surgical task acquired via the learner, and a reference image including at least one of an X-ray image, a Computed Tomography (CT) image, and a Magnetic Resonance Imaging (MRI) image.

The surgical robot system may further include a display unit that displays an endoscopic image corresponding to an image signal provided from an endoscope that is one kind of the auxiliary surgical tool.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
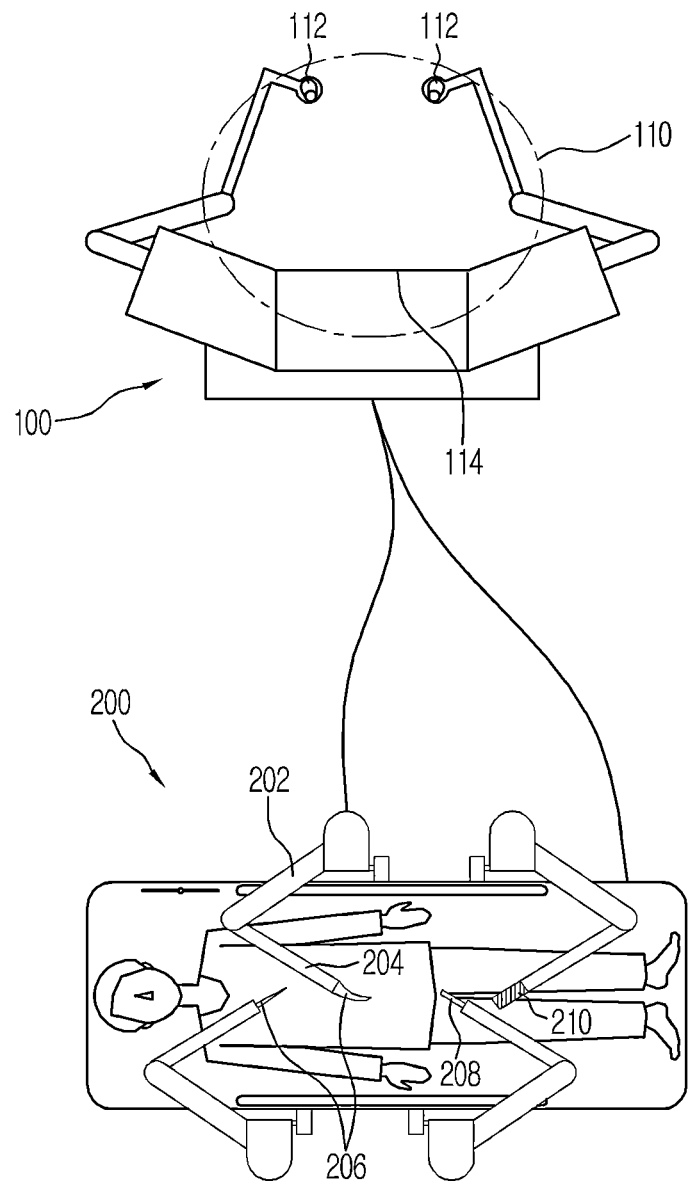
FIG. 1 is a plan view illustrating an overall configuration of a surgical robot system.

Reference will now be made in detail to the embodiments of the present invention, examples of which are illustrated in the accompanying drawings, wherein like reference numerals refer to like elements throughout.

Figure 2:
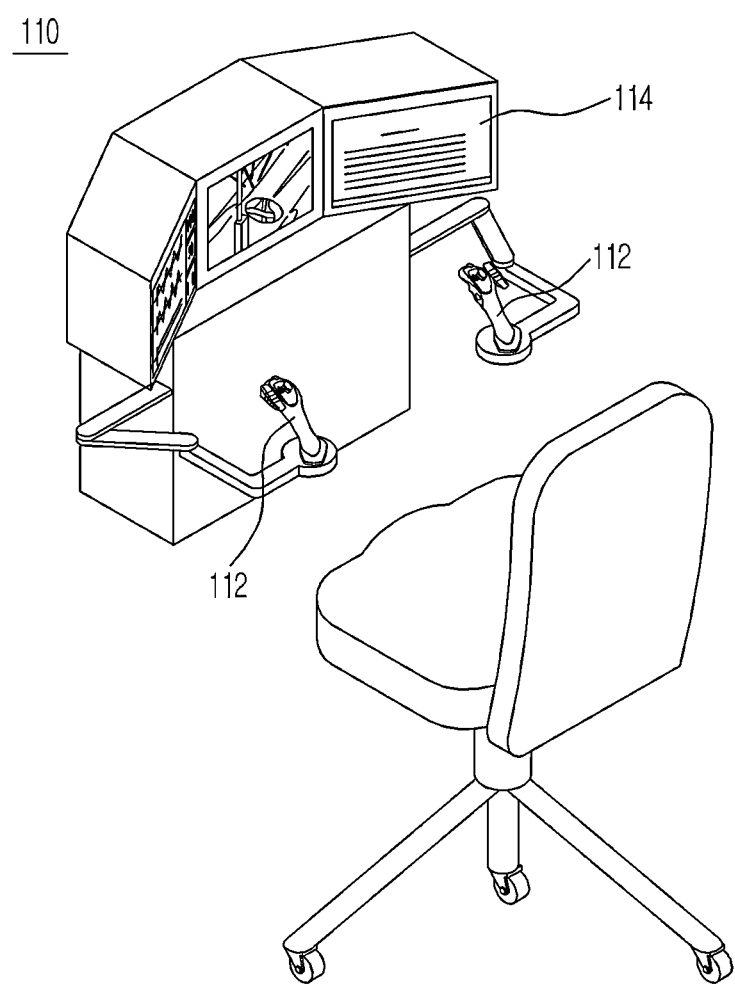
FIG. 2 is a conceptual view illustrating a master interface of the surgical robot system.

FIG. 1 is a plan view illustrating an overall configuration of a surgical robot system, and FIG. 2 is a conceptual view illustrating a master interface of the surgical robot system.

Referring to FIGS. 1 and 2, the surgical robot system includes a slave robot 200 that is used to perform an operation (e.g., a surgical operation) on an object (e.g., a patient who lies on an operating table), and a master robot 100 that assists an operator (e.g., a doctor) in remotely controlling the slave robot 200. The master robot 100 and the slave robot 200 are not essentially physically separate components, and may be integrated with each other. In this case, a master interface 110, for example, may correspond to an interface part of an integral robot. The slave robot 200 may be positioned in a surgery site as needed to perform a desired operation. For example, the slave robot 200 may be portable, may be fixed, or may be detachably disposed to a site (e.g., the railing of an operating table, or other object).

The master interface 110 of the master robot 100 may include master manipulators 112 and a display unit 114. The slave robot 200 may include robot arms 202, surgical instruments 204, surgical tools 206 and 208, and an endoscope 210.

The master interface 110 includes the master manipulators 112 that the operator grips and manipulates with both hands. The master interface 110 may also include a plurality of buttons, keys, and joysticks. Also, the master interface 110 may include an apparatus or device such as keyboard, pedal or footswitch, mouse, touchscreen, or voice control or microphone, to enable a user to control the surgical robot. The master interface 110 may further have additional features to assist the user in operating the surgical robot, including haptic feedback capability, head-mounted displays, virtual reality devices, or augmented virtual reality devices, for example. The master manipulators 112, as illustrated in FIGS. 1 and 2, may include two handles, for example. A control signal generated when the operator manipulates the handles is transmitted to the slave robot 200, which enables control of motions of the slave robot 200 including the robot arms 202, etc. The robot arms 202 may perform position-displacement, rotation, cutting, etc. in response to handle manipulation by the operator.

For example, the master manipulators 112 may include a main handle and a sub handle. Only one handle may be used to manipulate the robot arms 202, etc., or the sub handle may be added to enable real-time simultaneous manipulation using a plurality of surgical instruments. The main handle and the sub handle may include various mechanical configurations according to manipulation methods thereof, and for example, may include a joystick that performs 3-dimensional movement and various input devices to actuate the robot arms 202, surgical instruments 204, and surgical tools 206 and 208 of the slave robot 200.

The display unit 114 of the master interface 110 displays an image input by the endoscope 210.

The display unit 114 may include one or more monitors such that the respective monitors individually display data required for surgery. Although FIGS. 1 and 2 illustrate the display unit 114 as including three monitors, the number of monitors may be determined in various ways according to the type or kind of data to be displayed. The display unit 114 may be embodied by, for example, a Liquid Crystal Display (LCD), light emitting diode (LED) display, organic light emitting diode (OLED) display, plasma display panel (PDP), cathode ray tube (CRT), and the like.

The master robot 100 and the slave robot 200 may be coupled to each other via a wired or wireless communication network, or a combination thereof, and may transmit a control signal, e.g., an endoscopic image input through the endoscope 210 to the other party. When necessary to transmit two control signals corresponding to the two handles provided at the master interface 110, e.g., when a control signal for position adjustment of the surgical tools 206 and 208 coupled to the surgical instruments 204 and a control signal for position adjustment of the endoscope 210 coupled to the surgical instrument 204 are transmitted simultaneously or at similar times, the respective control signals may be transmitted independently of each other to the slave robot 200.

Here, "independent" transmission of the respective control signals refers to no interference between the control signals, and that any one control signal has no effect on the other signal. To ensure independent transmission of the plurality of control signals, various methods, for example, transmission of additional header data regarding the respective control signals, transmission of the respective signals based on a generation sequence thereof, or transmission of the control signals based on a preset order of priority, may be used. In this case, it may be possible to fundamentally prevent interference between the respective control signals by providing independent transmission paths of the respective signals.

The robot arms 202 of the slave robot 200 may be driven with multiple degrees of freedom. The surgical instruments 204 may be mounted to ends of the robot arms 202 respectively. The various surgical tools 206 and 208 which may be used to perform a surgical operation, such as a skin holder, a suction line, an effector, etc., and the endoscope 210 may be mounted to ends of the surgical instruments 204 for implementation of surgery. The surgical tools may also include, for example, a needle holder, micro-dissector, staple applier, tacker, suction irrigation tool, clip applier, cutting blade, irrigator, catheter, suction orifice, surgical knife, surgical forceps, scissors, a cautery (a tool for burning or cutting a diseased part by using electric energy or heat energy), and the like.

The surgical tools may be basically classified into a main surgical tool 206 and an auxiliary surgical tool 208. The main surgical tool 206 refers to a tool that performs direct surgical motions, such as, e.g., cutting and suturing on a surgical part (e.g., a knife or a surgical needle). The auxiliary surgical tool 208 refers to a tool that does not perform direct motions on a surgical part and assists motion of the main surgical tool 206 (e.g., a skin holder). Likewise, the endoscope 210 does not perform direct motions on a surgical part and is used to assist a motion of the main surgical tool 206. Therefore, the endoscope 210 may be considered as corresponding to the auxiliary surgical tool in a broad sense.

The endoscope 210 may be selected from among various surgical endoscopes, such as a thoracoscope, an arthroscope, and a rhinoscope, in addition to a celioscope that is mainly used in robotic surgery.

Although FIG. 1 illustrates the slave robot 200 having multiple ports, multiple robot arms, multiple surgical instruments, and multiple surgical tools by way of example, additionally, the embodiment may be applied to a surgical robot system including a slave robot having a single-port, multiple robot arms, multiple surgical instruments, and multiple surgical tools, a slave robot having a single port, a single robot arm, multiple surgical instruments, multiple surgical tools, and various other slave robots having different configurations.

Figure 3:
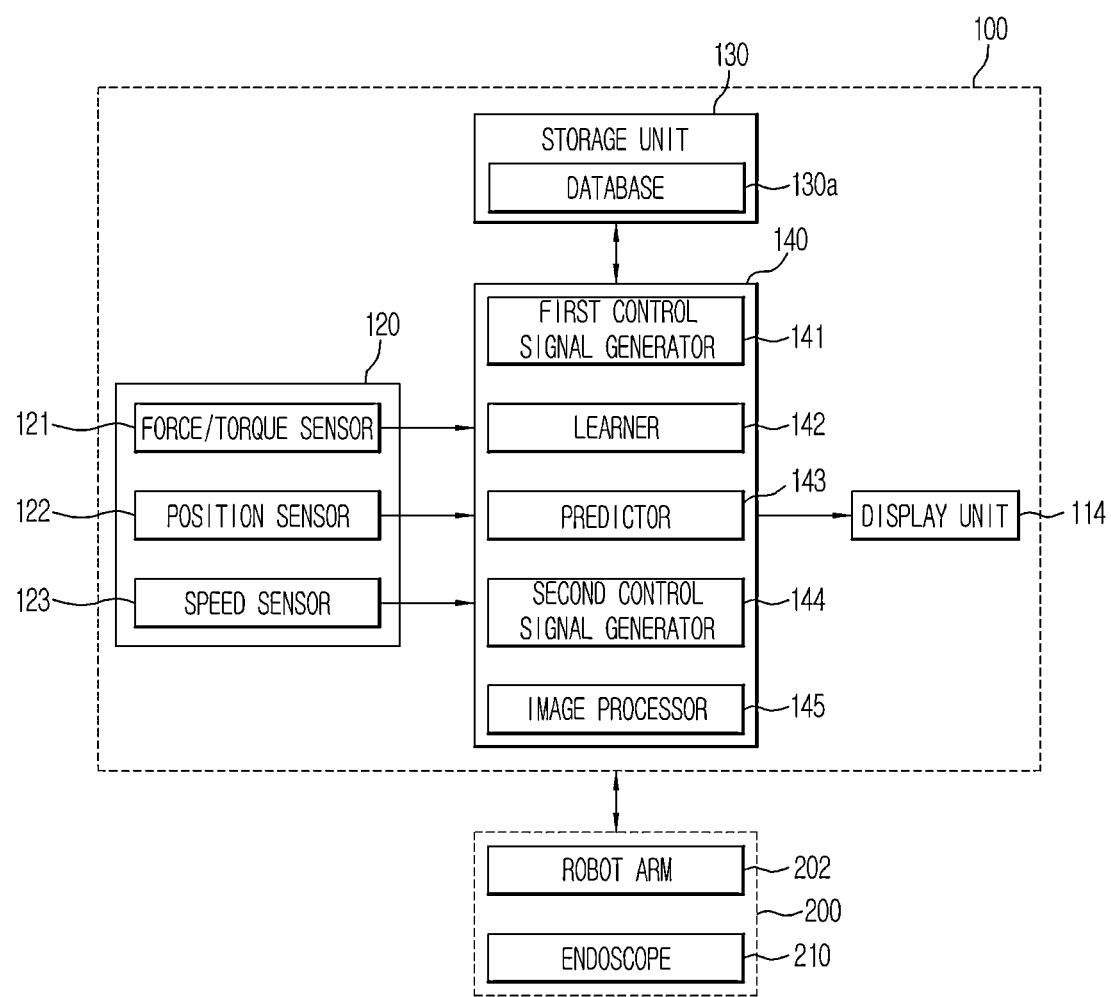
FIG. 3 is a control block diagram of the surgical robot system.

FIG. 3 is a control block diagram of the surgical robot system.

As illustrated in FIG. 3, the master robot 100 may include a motion data detector 120, a storage unit 130, a controller 140, and the display unit 114. The slave robot 200 may include the robot arms 202 and the endoscope 210.

The motion data detector 120 may be mounted to the master manipulator 112 that assists the operator in manipulating or controlling the robot arms 202 of the slave robot. For example, the operator may manipulate positions and functions of the robot arms 202 of the slave robot 200, and the motion data detector 120 serves to detect a motion of the master manipulator 112. The motion data detector 120 may include a force/torque sensor 121 that detects an interactive force F between the master manipulator 112 and the operator, a position sensor 122 that detects a position x of the master manipulator 112, and a speed sensor 123 that detects a speed v of the master manipulator 112. The position sensor 122 may be selected from among a motor encoder and various other measurement devices. The speed sensor 123 may be, for example, a tachometer. Although FIG. 3 illustrates the case of detecting a speed of the master manipulator 112 using the speed sensor 123 by way of example, the speed of the master manipulator 112 may be calculated via differentiation of an output value of a motor encoder, without using the speed sensor 123.

The storage unit 130 may include a memory device that stores a database 130a in which results of learning performed by a learner 142 are stored. The database 130a further stores training data used for learning and weighting values w determined by the learning results.

The storage unit 130 may store various images, such as X-ray images, Computed Tomography (CT) images, Magnetic Resonance Imaging (MRI) images, etc., captured before surgery. The storage unit 130 may also store images captured during an operation of the surgical robot (e.g., images captured by the endoscope during surgery). The storage unit 130 may include a storage medium, such as a nonvolatile memory device, such as a Read Only Memory (ROM), Programmable Read Only Memory (PROM), Erasable Programmable Read Only Memory (EPROM), and flash memory, a volatile memory device such as a Random Access Memory (RAM), a hard disc, and an optical disc, or combinations thereof. However, examples of the storage unit are not limited to the above description, and the storage unit may be realized by other various devices and structures as would be understood by those skilled in the art.

The controller 140 may include a processor to control general motions of the surgical robot system. The controller 140 may include a first control signal generator 141, the learner 142, a predictor 143, a second control signal generator 144, and an image processor 145.

The first control signal generator 141 generates a first control signal to control motions of the slave robot 200 (i.e. motions of the main surgical tools 206, the auxiliary surgical tools 208, and/or the endoscope 210) based on the data regarding a motion of the master manipulator 112 acquired via the motion data detector 120.

The learner 142 learns a plurality of motions constituting a surgical task based on the data regarding a motion of the master manipulator 112 acquired before surgery.

Conventionally, examples of surgical tasks performed by the operator (e.g., a doctor) during surgery include suturing, passing, running, and cannulation. Each surgical task may generally include or follow five motions, i.e. a combination of a reach motion (see ① of FIG. 4), an orient or rotate motion (see ② of FIG. 4), a grasp motion, a push motion (see ③ of FIG. 4), and a pull motion (see ④ of FIG. 4). In general, the orient motion is mainly used when inserting and picking out a surgical needle, and the push/pull motion is mainly used when manipulating a surgical thread within an appropriate surgical range. The five motions may be used in robotic surgery. Here, the grasp motion is easily detected based on an open or closed state of a grasper. The reach motion is similar to the push/pull motion, and only one difference therebetween is a movement direction of the main surgical tools 206, the auxiliary surgical tools 208, and/or the endoscope 210 manipulated by the master manipulators 112. That is, the movement direction may serve as a criterion for distinction between the reach motion and the push/pull motion. In this case, the pull motion refers to a direction toward the operator, and the push motion refers to a direction opposite to that of the pull motion.

Accordingly, a following description of the present embodiment is focused only on three motions (orient, push, and pull motions). However, additional motions may be employed as necessary.

The predictor 143 predicts basic motions to be performed by the operator based on the data regarding a motion detected by the motion data detector 120 and the results of learning performed by the learner 142. In addition, the predictor 143 sequentially connects the predicted basic motions to one another, thereby predicting a surgical task that the operator wishes to perform.

The second control signal generator 144 generates a second control signal to control motions of the slave robot 200 and/or the master manipulators 112 having a redundant degree of freedom (DOF) based on the basic motions or the surgical task predicted by the predictor 143.

The image processor 145 processes an input endoscopic image from the endoscope 210 that is an example or type of auxiliary surgical tool, to output a picture image.

The display unit 114 outputs the picture image corresponding to the endoscopic image input from the endoscope 210 of the slave robot 200, or visual data including various reference images, such as X-ray images, CT images, MRI images, etc., that are captured before surgery and may be stored in the storage unit 130.

Figure 5:
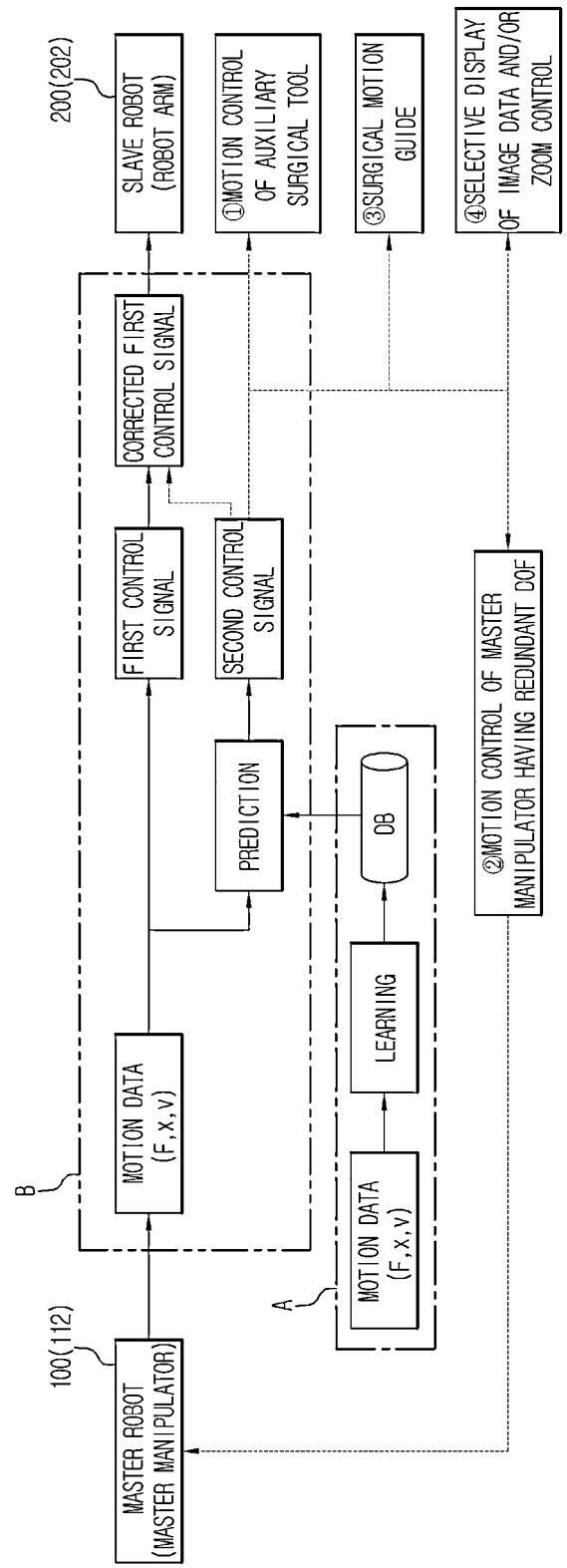
FIG. 5 is a conceptual view explaining an overall control algorithm of the surgical robot system.

FIG. 5 is a conceptual view explaining an overall control algorithm of the surgical robot system according to an embodiment of the present invention.

Area "A" illustrated in FIG. 5 (the area designated by a dot-dashed line in FIG. 5) represents an off-line process (learning) that is performed before surgery, and area "B" represents an on-line process (generation of a control signal for a general slave robot and generation of a control signal based on a motion predicted using the learning results) that is performed during surgery.

Figure 4:
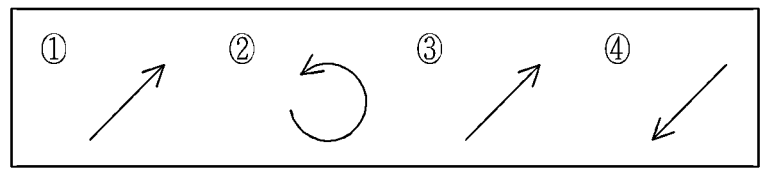
FIG. 4 is a view illustrating a plurality of motions constituting a surgical task.

First, referring to the area "A" of FIG. 5, prior to performing surgery, as the operator of the master manipulator 112 (e.g., an employee of a manufacturer of the surgical robot system or a doctor using the surgical robot system) manipulates the master manipulator 112 according to a plurality of motions constituting a surgical task (e.g., orient, push, and pull motions of the present embodiment, see FIG. 4), data regarding a motion of the master manipulator 112, are acquired. Data regarding the motion of the master manipulator 112 may include, for example, interactive force data F between the operator and the master manipulator 112, position data x of the master manipulator 112, and speed data v of the master manipulator 112. After learning the plurality of motions constituting the surgical task based on the acquired motion data (e.g., F, x and v), learning results are stored in the database 130a.

Next, referring to the area "B" of FIG. 5, if surgery is initiated and the operator of the master manipulator 112 (e.g., a doctor using the surgical robot system) manipulates the master manipulator 112 to perform a surgical motion, data regarding the motion of the master manipulator 112 is acquired. A first control signal to control motions of the main surgical tools 206, the auxiliary surgical tools 208, and/or the endoscope 210 that the operator wishes to manipulate is generated based on the acquired motion data.

A basic motion to be performed by the operator is predicted using the data regarding the motion of the master manipulator 112 acquired during surgery and the results of learning stored in the database 130a during the above-described learning procedure. Here, prediction of the operator basic motion may be prediction of each of a plurality of motions constituting a surgical task, or may be prediction of a surgical task constituted by sequential connection of a plurality of predicted operator basic motions.

A second control signal to control motions of the slave robot 200 (the main surgical tools 206, the auxiliary surgical tools 208, and/or the endoscope 210) and/or the master manipulators 112, may be generated based on the predicted basic motion or surgical task.

By using the second signal generated based on the predicted motions, for example, ① motion control of the auxiliary surgical tools (including the endoscope), ② motion control of the master manipulator 112 having a redundant DOF, ③ motion guidance for safe surgery, and ④ selective display and/or zoom control of image data, may be performed.

Here, motion control of the auxiliary surgical tools refers to adjustment of the auxiliary surgical tools, such as a skin holder or the endoscope, i.e. movement or fixing of the auxiliary surgical tools to or at an optimized position based on the operator motion predicted as described above (e.g., the basic motion and the surgical task).

Motion control of the master manipulator 112 having a redundant DOF refers to controlling the master manipulator 112 having a redundant DOF based on the operator motion predicted as described above (e.g., the basic motion and the surgical task) to allow the operator to more comfortably manipulate the master manipulator 112.

Motion guidance for safe surgery may refer to controlling the main surgical tools 206, the auxiliary surgical tools 208, and/or the endoscope 210 so as not to invade a particular region of an object or a patient (e.g., a human body), based on the operator motion predicted as described above (e.g., the basic motion and the surgical task). The particular region may include, for example, a region in which important organs (e.g., heart and stomach) or blood vessels are located (the particular region may be defined by a virtual wall).

Alternatively, motion guidance for safe surgery may refer to providing or outputting a warning (e.g., by displaying a warning message) to the operator (e.g., a doctor) when the main surgical tools 206, the auxiliary surgical tools 208, and/or the endoscope 210 attempt to enter the particular region of the human body or object, based on the operator motion predicted as described above (e.g., the basic motion and the surgical task). By way of further example, a warning may be generated by one or more different devices (e.g., an alarm may be output to a user via a vibration or other tactile feedback, sound, visual warnings such as a lamp or message, or other physical indicator to warn the user). Here, to control the main surgical tools 206, the auxiliary surgical tools 208, and/or the endoscope 210 so as not to invade the particular region of the human body, a corrected first control signal may be generated by combining the first control signal to control motions of the main surgical tools 206, the auxiliary surgical tools 208, and/or the endoscope 210 that the operator wishes to manipulate with the second signal generated based on the predicted motion, such that the slave robot 200 is controlled by the corrected first control signal.

Selective display and/or zoom control of image data refers to selectively providing image data suitable for the operator motion predicted as described above (the basic motion and the surgical task). More specifically, selective display of image data may include selecting image data suitable for the predicted motion from among X-ray images, CT images, MRI images, and endoscopic images, and displaying the selected image data on the display unit. In addition, zoom control of image data may refer to zoom-in/zoom-out via variation in the focal length of a zoom lens provided in the endoscope 210.

Hereinafter, a procedure of learning a plurality of motions constituting a surgical task will be described with reference to FIGS. 6 to 8.

Figure 6:
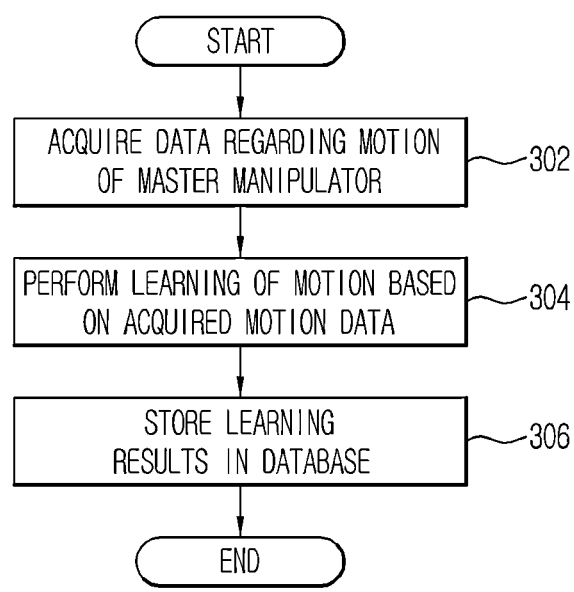
FIG. 6 is a flowchart illustrating a learning procedure of the overall control algorithm of the surgical robot system.
Figure 7:
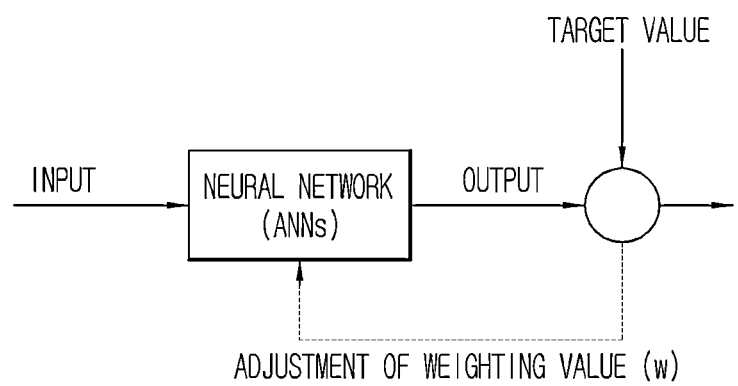
FIG. 7 is a view explaining the concept of supervised learning using artificial neural networks (ANNs)
Figure 8:
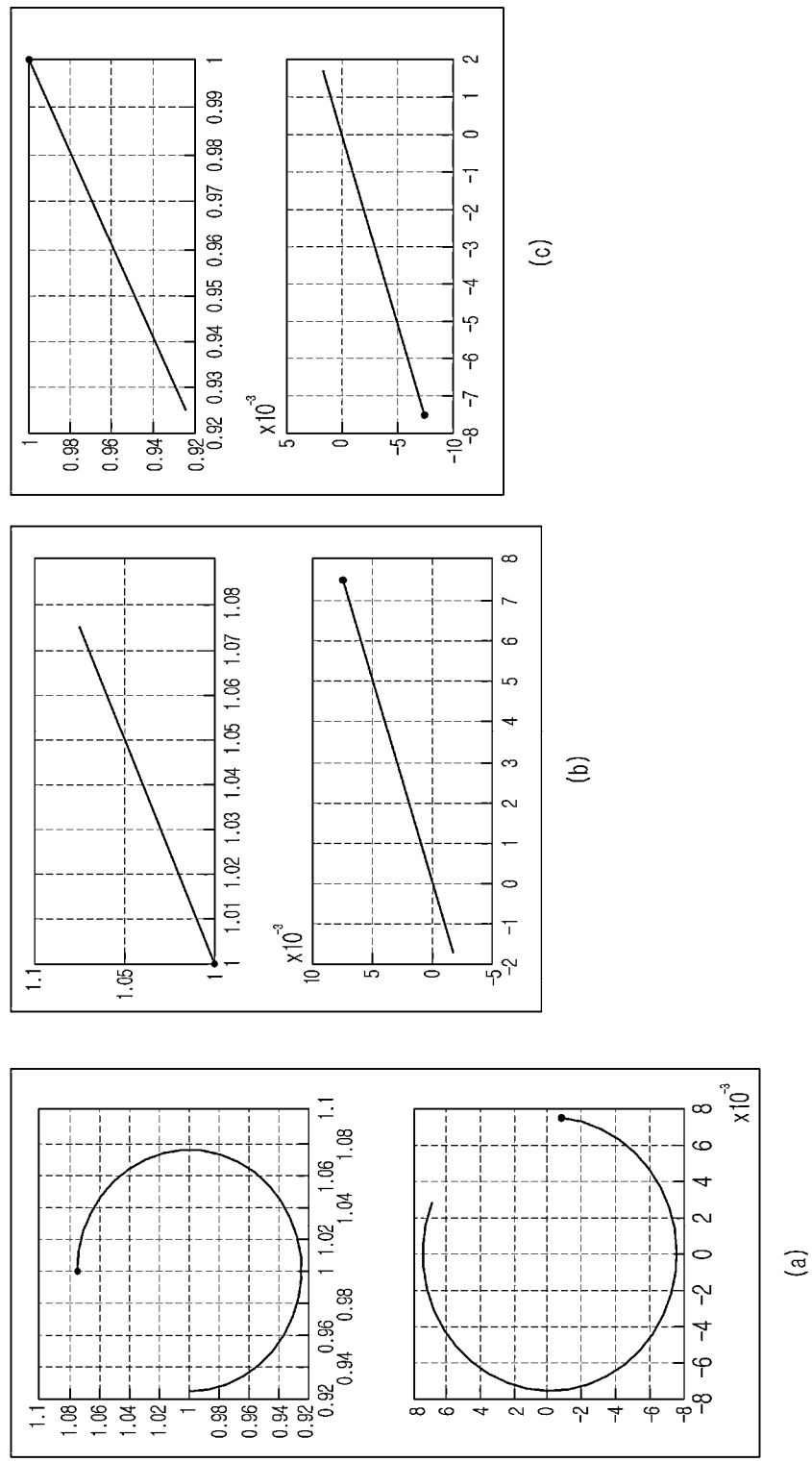
FIG. 8 is a view illustrating training data on an orient motion, a push motion, and a pull motion.

FIG. 6 is a flowchart illustrating a learning procedure of the overall control algorithm of the surgical robot system, FIG. 7 is a view explaining the concept of supervised learning using artificial neural networks (ANNs), and FIG. 8 is a view illustrating training data on an orient motion, a push motion, and a pull motion.

Explaining a learning procedure of the overall control algorithm of the surgical robot system with reference to FIG. 6, first, prior to performing surgery, the operator of the master manipulator 112 (e.g., an employee of a manufacturer of the surgical robot system or a doctor using the surgical robot system) manipulates the master manipulator 112 according to a plurality of motions constituting a surgical task (e.g., orient, push, and pull motions). In this case, a motion that the operator performs via the master manipulator 112 is referred to as a target motion. Here, assuming that an orient motion that may become the target motion is similar to a circle drawing motion, the operator may manipulate the master manipulator 112 according to various orient motions, such as an orient motion of drawing a plurality of circles having different radii, or an orient motion of drawing circles in different planes, e.g., in the XY plane and the YZ plane. Since it may be possible for the operator to manipulate the master manipulator 112 in various ways through a single motion (e.g., an orient motion), a greater quantity of training data depending on the motion may be acquired, which improves prediction accuracy with respect to the motion.

Once the operator of the master manipulator 112 has manipulated the master manipulator 112 according to the plurality of motions constituting the surgical task, the motion data detector 120 detects data regarding the motion of the master manipulator 112, and transmits the detected data to the controller 140 (302). Here, the data regarding the motion of the master manipulator 112 may include interactive force data F between the master manipulator 112 and the operator, position data x of the master manipulator 112, and speed data v of the master manipulator 112. In addition, the data may include various other data that may indicate the motion of the master manipulator 112 (e.g., acceleration data of the master manipulator 112).

The learner 142 included in the controller 140 learns the plurality of motions constituting the surgical task based on the motion data (e.g., F, x, v) acquired from the motion data detector 120 (304).

Machine learning for the basic motion to predict the operator motion using the master manipulator 112 may include supervised learning useful for pattern classification and prediction of input data, and unsupervised learning useful for grouping and separation of input data. Here, machine learning serves to analogize one function from training data.

As the machine learning for the plurality of motions constituting the surgical task to predict the operator motion using the master manipulator 112, the case of using supervised learning that is performed in a state in which a target result value for an input value (target value) is given will be described by way of example.

In supervised learning, generally, artificial neural networks (ANNs) or Baysian networks are used. Here, in particular, the case of learning basic motions via supervised learning using ANNs will be described by way of example.

As illustrated in FIG. 7, an ANN processes input data. Training data is input to the input side of the ANN. In this case, training data may include the detected motion data (e.g., F, x, v) from the motion data detector 120 with regard to a target motion of the operator using the master manipulator 112. For example, if the target motion of the operator is an orient motion, training data as illustrated in FIG. 8(a) is input to the ANN, and if the target motion of the operator is a push motion, training data as illustrated in FIG. 8(b) is input to the ANN. Also, if the target motion of the operator is a pull motion, training data as illustrated in FIG. 8(c) is input to the ANN. Here, position data x of the master manipulator 112 is illustrated at the upper portions of FIGS. 8(a), 8(b) and 8(c), and interactive force data F between the master manipulator 112 and the operator is illustrated at the lower portions of FIGS. 8(a), 8(b) and 8(c).

An output value of the ANN may be a function of adding a variable weighting value w to an input value. An error between a calculated output value and a target value is used to adjust the weighting value w. In this case, the target value is set based on the target motion of the operator (e.g., the orient motion). For example, a target value of the orient motion may be set to 1, a target value of the push motion may be set to 2, and a target value of the pull motion may be set to 3. If the operator inputs the orient motion in a plurality of forms, the same target value of 1 is set with respect to the plurality of orient motions. Here, an output value suitable for a particular input value may be acquired by changing the weighting value w. A procedure of adjusting the weighting value w is referred to as learning. That is, the weighting value w is calculated as a result of supervised learning using ANNs.

Returning to a description with regard to FIG. 6, the learner 142 stores the results of learning the plurality of motions constituting the surgical task (training data and weighting value w in the case of supervised learning using ANNs) in the database 130a of the storage unit 130, and ends the learning procedure (306).

Hereinafter, a procedure of predicting an operator motion using the master manipulator based on learning results will be described with reference to FIGS. 9 to 11.

Figure 9:
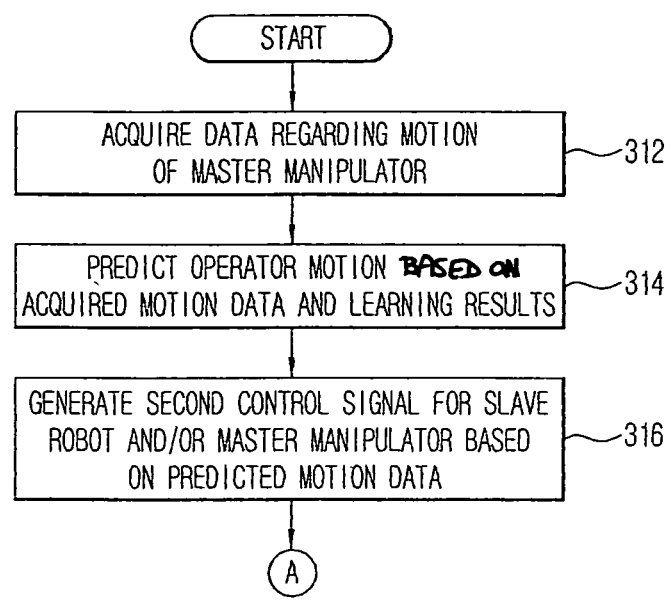
FIG. 9 is a flowchart illustrating a prediction procedure of the overall control algorithm of the surgical robot system.
Figure 10:
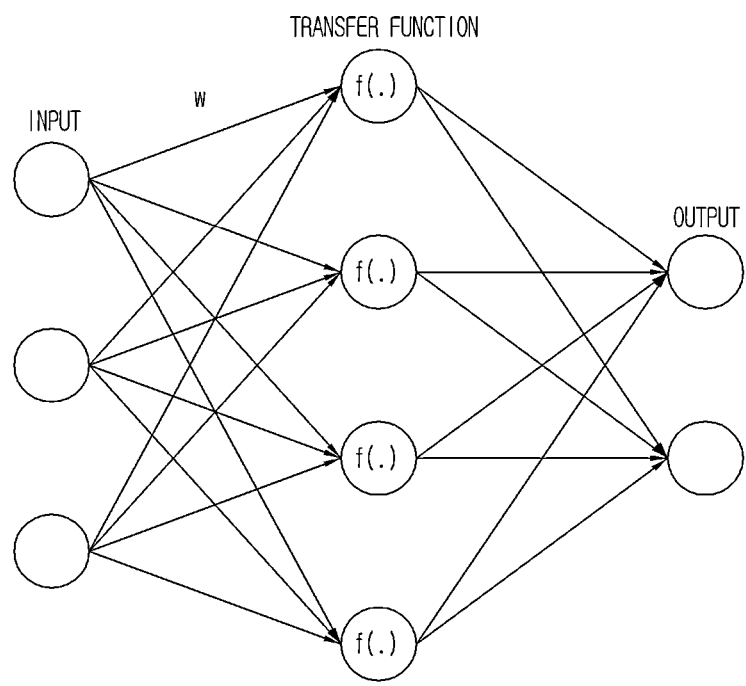
FIG. 10 is a view explaining the concept of output prediction based on results of supervised learning.
Figure 11:
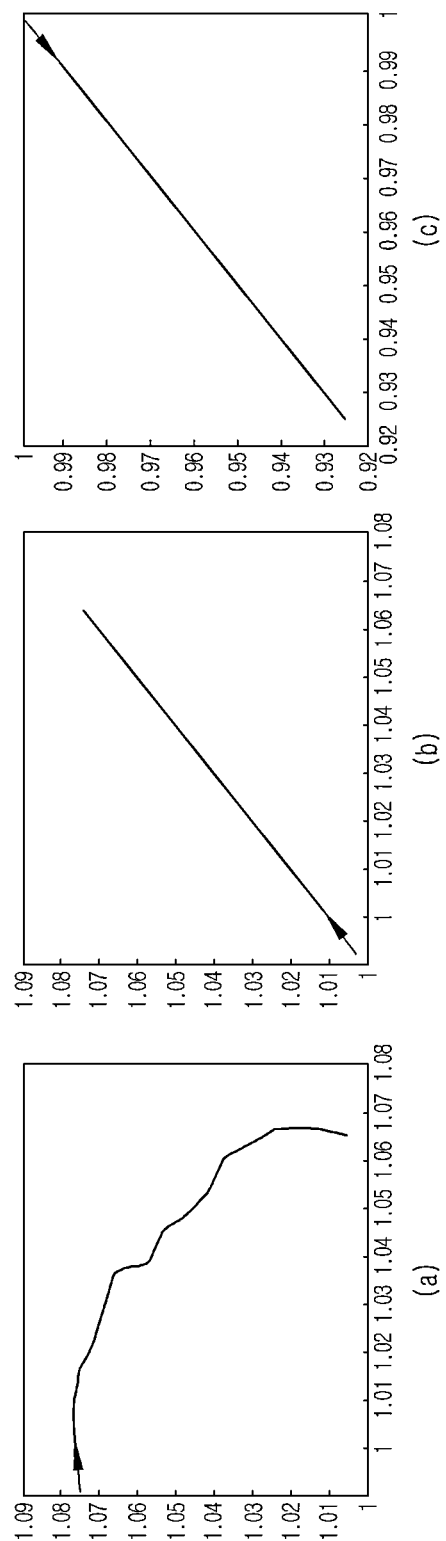
FIG. 11 is a view illustrating prediction data regarding an orient motion, a push motion, and a pull motion.

FIG. 9 is a flowchart illustrating a prediction procedure of the overall control algorithm of the surgical robot system, FIG. 10 is a view explaining the concept of output prediction based on results of supervised learning, and FIG. 11 is a view illustrating prediction data regarding an orient motion, a push motion, and a pull motion.

Explaining the prediction procedure of the overall control algorithm of the surgical robot system with reference to FIG. 9, first, the operation (e.g., performing a surgery) is initiated and the operator of the master manipulator 112 (e.g., a doctor who uses the surgical robot system) performs a given motion (surgical motion) via the master manipulator 112.

When the operator performs the given surgical motion via the master manipulator 112, the motion data detector 120 detects data regarding the motion of the master manipulator 112, and transmits the detected data to the controller 140 (312). The data regarding the motion of the master manipulator 112 may include interactive force data F between the master manipulator 112 and the operator, position data x of the master manipulator 112, and speed data v of the master manipulator 112. In addition, the data may include various other data that may indicate the motion of the master manipulator 112 (e.g., acceleration data of the master manipulator 112).

The predictor 143 included in the controller 140 predicts an operator motion using the master manipulator 112 based on the motion data (e.g., F, x, V) acquired from the motion data detector 120 and the learning results illustrated in FIG. 6 (314). In this case, the predicted operator motion may include a plurality of motions constituting a surgical task, and a surgical task constituted by sequential connection of predicted basic motions.

The case of predicting the operator motion based on results of supervised learning using the above-described artificial neural network will hereinafter be described by way of example.

As illustrated in FIG. 10, the artificial neural network, which is composed of weighting values w calculated as learning results and a transfer function, processes input data. Prediction data is input to the input side of the artificial neural network. In this case, the prediction data may include motion data (e.g., F, x, v) detected via the motion data detector 120 regarding a motion that the operator performs via the master manipulator 112 for surgery.

For example, if the operator's surgical motion is an orient motion, prediction data as illustrated in FIG. 11(a) is input to the artificial neural network. If the operator's surgical motion is a push motion, prediction data as illustrated in FIG. 11(b) is input to the artificial neural network. If the operator's surgical motion is a pull motion, prediction data as illustrated in FIG. 11(c) is input to the artificial neural network. FIGS. 11(a), 11(b) and 11(c) illustrate position data x of the master manipulator 112.

An output of the artificial neural network is calculated by applying a weighting value w calculated as the results of learning and by applying the transfer function to the input data. For example, assuming that a target value of the orient motion is set to 1, a target value of the push motion is set to 2, and a target value of the pull motion is set to 3 during learning, if data regarding three types of orient motions as prediction data is input to the input side of the artificial neural network illustrated in FIG. 10, a derived output value is 1. If data regarding two types of orient motions and one type of a push motion as prediction data is input to the input side of the artificial neural network illustrated in FIG. 10, derived output values are 1 and 2.

Returning to a description with regard to FIG. 9, the predictor 143 transmits the operator motion predicted as described above to the second control signal generator 144 included in the controller 140.

Thereafter, the second control signal generator 144 generates a second control signal to control motions of the slave robot 200 and/or the master manipulator 112 (if the master manipulator has a redundant DOF) based on the operator motion predicted by the predictor 143 (e.g., the basic motion or the surgical task) (316).

Figure 12:
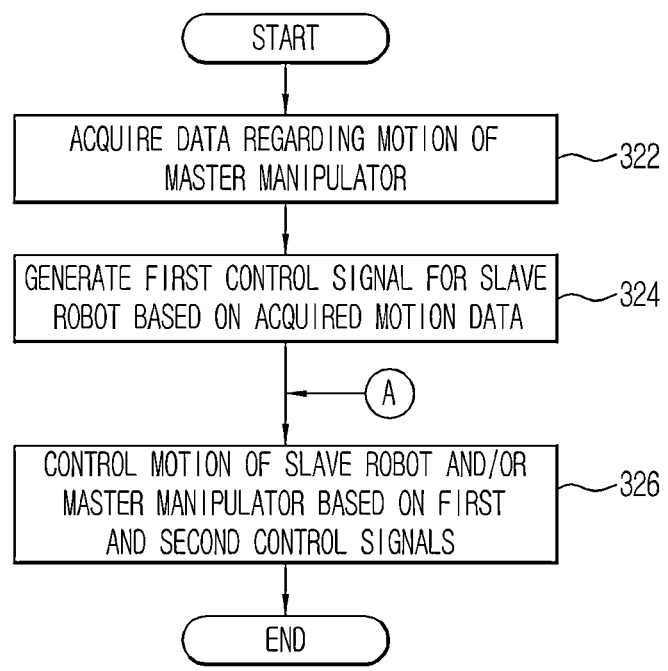
FIG. 12 is a flowchart illustrating a control method of the surgical robot system.

FIG. 12 is a flowchart illustrating a control method of the surgical robot system.

When the operator performs a given surgical motion via the master manipulator 112, the motion data detector 120 detects data regarding the motion of the master manipulator 112, and transmits the detected data regarding the motion of the master manipulator 112 to the controller 140 (322). Although FIGS. 9 and 12 are separately provided for differentiated description between the procedure of predicting the operator motion and the general control procedure of the surgical robot system, Operation 322 of FIG. 12 corresponds to Operation 312 of FIG. 9.

Next, the first control signal generator 141 included in the controller 140 generates a first control signal to control motions of the slave robot 200 i.e., motions of the main surgical tools 206 and/or the auxiliary surgical tools 208, and/or the endoscope 210) based on the motion data (e.g., F, x, v) acquired from the motion data detector 120 (324).

The controller 140 controls motions of the slave robot 200 and/or the master manipulator 112 (e.g., if the master manipulator has a redundant DOF) based on the first control signal generated in Operation 324 and a second control signal generated in Operation 316 of FIG. 9 (326).

Figure 13:
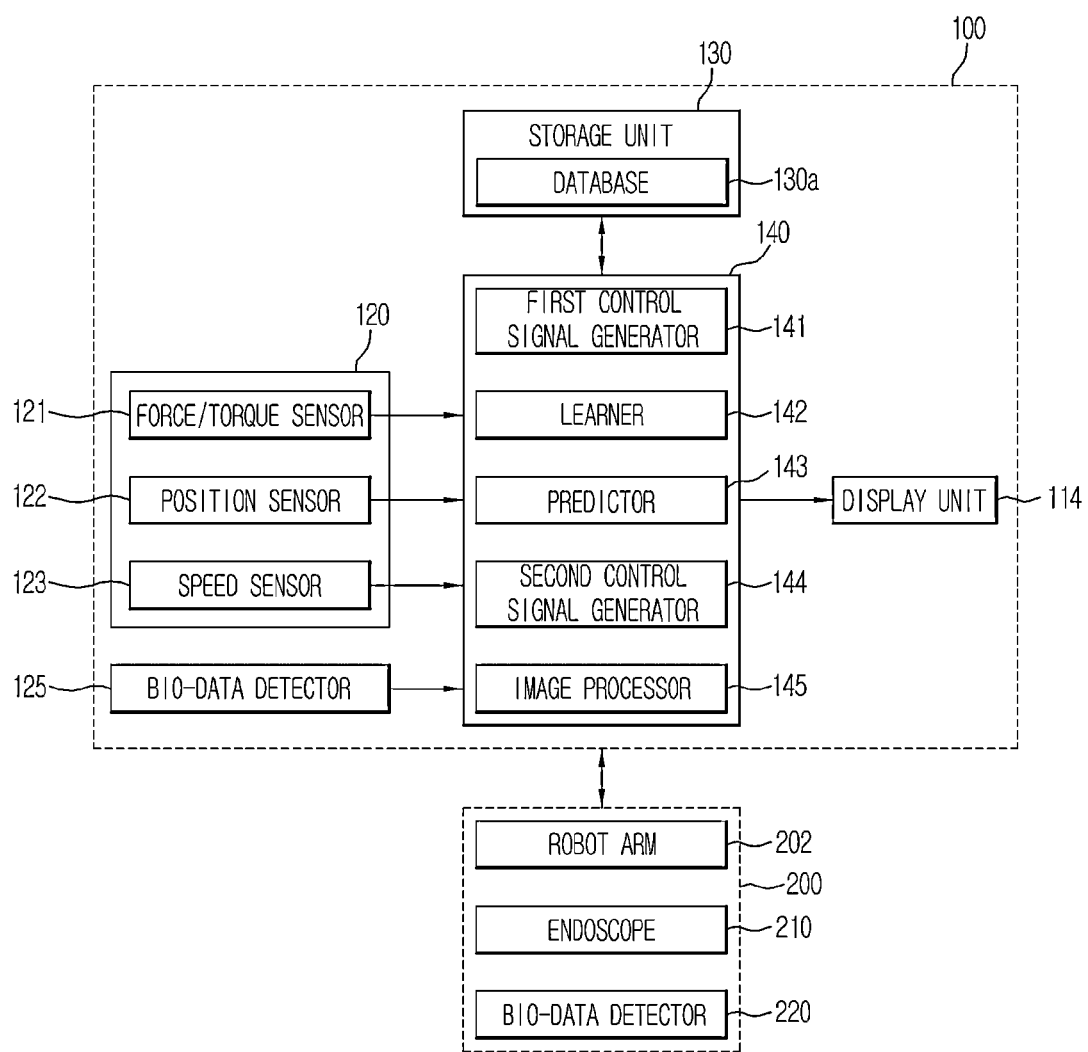
FIG. 13 is a control block diagram of the surgical robot system.

FIG. 13 is a control block diagram of the surgical robot system.

As illustrated in FIG. 13, when compared with the surgical robot system of FIG. 3, the surgical robot system differs from the surgical robot system of FIG. 3 in terms of a bio-data detector 125 added to the input side of the controller 140 of the master robot 100 and a bio-data detector 220 added to the slave robot 200.

Here, for the sake of brevity, a description of constituent elements represented by the same names and same reference numerals is omitted, and only configurations of the bio-data detectors 125 and 220 additionally illustrated in FIG. 13 will be described.

The bio-data detector 125 of the master robot 100 may be installed at one side of the master manipulator 112 and serves to detect bio-data of the operator of the master manipulator 112 (e.g., a doctor). Here, bio-data of the operator may include a heart rate for discrimination of the level of tension of the operator. The bio-data detector 125 may include a measurement module for discrimination of the level of tension of the operator, such as a heart-rate measurement module.

The bio-data detector 220 of the slave robot 200 serves to detect bio-data of a patient, and transmits the detected bio-data of the patient to the master robot 100. The bio-data detector 220 of the slave robot 200 may include one or more modules among an electrocardiography (ECG) measurement module, a blood-pressure measurement module, a breathing-rate measurement module, a body-heat measurement module, and a heart-rate measurement module. The bio-data of the patient measured by each module may be transmitted, as analog signals or digital signals, from the slave robot 200 to the master robot 100. The master robot 100 may display the received bio-data via the display unit 114.

The display unit 114 of the master robot 100 may display a plurality of bio-data of the patient. In this case, an index representing the state of the patient, for example, an ECG, blood-pressure, breathing-rate, body-heat, and heart-rate, may be output via one or more monitors of the display unit 114, and each data may be displayed on a per region basis.

Figure 14:
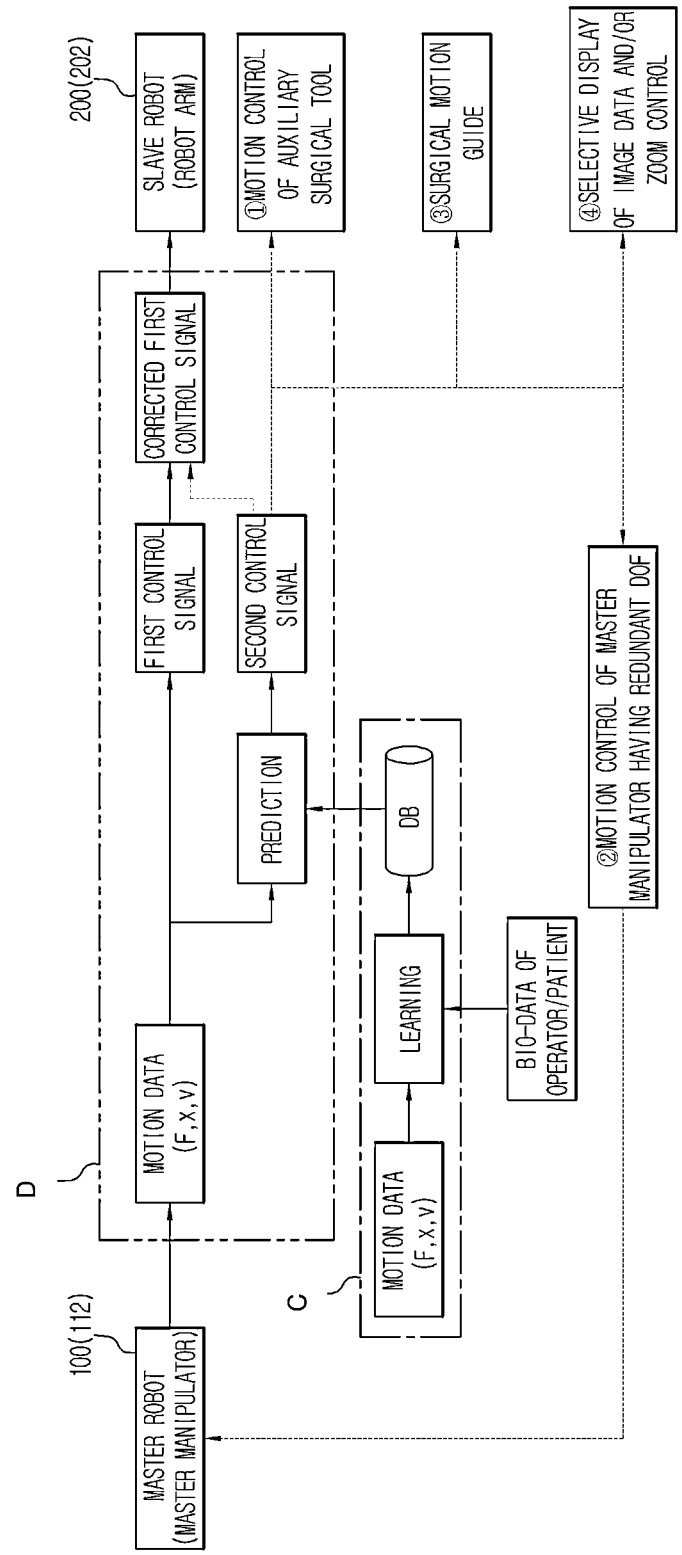
FIG. 14 is a conceptual view explaining an overall control algorithm of the surgical robot system.

FIG. 14 is a conceptual view explaining an overall control algorithm of the surgical robot system.

Area "C" illustrated in FIG. 14 (the area designated by a dot-dashed line in FIG. 14) represents an off-line process (learning) that is performed before surgery, and area "D" represents an on-line process (generation of a control signal for a general slave robot and generation of a control signal based on motions predicted using results of learning) that is performed during surgery.

First, referring to the area "C" of FIG. 14, prior to performing surgery, as the operator of the master manipulator 112 (e.g., an employee of a manufacturer of the surgical robot system or a doctor using the surgical robot system) manipulates the master manipulator 112 according to a plurality of motions constituting a surgical task (e.g., orient, push, and pull motions of the present embodiment, as shown in FIG. 4 for example), data regarding a motion of the master manipulator 112, are acquired. For example, data regarding a motion of the master manipulator 112 may include interactive force data F between the operator and the master manipulator 112, position data x of the master manipulator 112, and speed data v of the master manipulator 112. Bio-data of the operator and/or patient (simulated patient) may also be obtained prior to performing a surgery, for example in a training session. After learning the plurality of motions constituting the surgical task based on the acquired motion data (e.g., F, x, v, and bio-data of the operator and/or patient), learning results are stored in the database 130a.

Next, referring to the area "D" of FIG. 14, if surgery is initiated and the operator of the master manipulator 112 (e.g., a doctor using the surgical robot system) manipulates the master manipulator 112 to perform a surgical motion, data regarding the motion of the master manipulator 112 is acquired. A first control signal to control motions of the main surgical tools 206, the auxiliary surgical tools 208, and/or the endoscope 210 that the operator wishes to manipulate is generated based on the acquired motion data (e.g., F, x, v).

An operator motion is predicted using the data regarding the motion of the master manipulator 112 acquired during surgery, bio-data of the operator/patient acquired during surgery, and the learning results stored in the database 130a. Here, prediction of the basic motion to be performed by the operator may be prediction of each of a plurality of motions constituting a surgical task, or may be prediction of a surgical task constituted by sequential connection of a plurality of predicted basic motions.

A second control signal to control motions of the slave robot 200 (the main surgical tools 206, the auxiliary surgical tools 208, and/or the endoscope 210) and/or the master manipulator 112, is generated based on the predicted basic motion or surgical task.

By using the second control signal generated based on the predicted motion, for example, ① motion control of the auxiliary surgical tools (including the endoscope), ② motion control of the master manipulator 112 having redundant DOF, ③ motion guidance for safe surgery, and ④ selective display and/or zoom control of image data may be performed.

Figure 15:
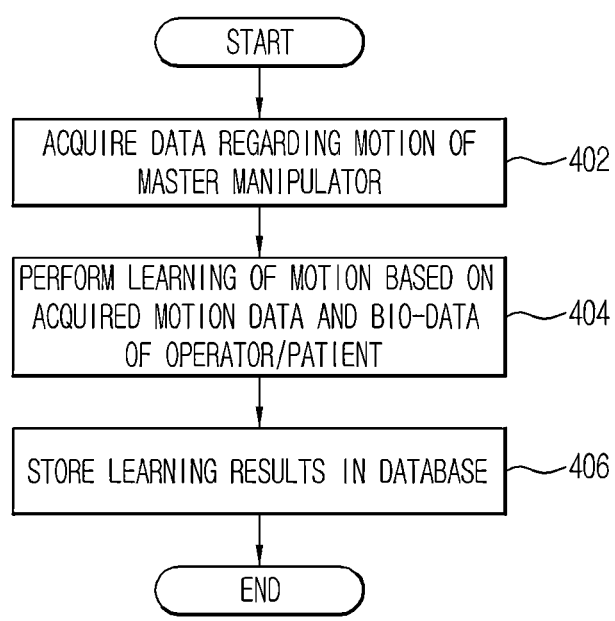
FIG. 15 is a flowchart illustrating a learning procedure of the overall control algorithm of the surgical robot system.

Explaining a learning procedure of the overall control algorithm of the surgical robot system with reference to FIG. 15, first, prior to performing surgery, the operator of the master manipulator 112 (e.g., an employee of a manufacturer of the surgical robot system or a doctor using the surgical robot system) manipulates the master manipulator 112 according to a plurality of motions constituting a surgical task (e.g., orient, push, and pull motions). Once the operator of the master manipulator 112 has manipulated the master manipulator 112 according to the plurality of motions constituting a surgical task, the motion data detector 120 detects data regarding the motion of the master manipulator 112, and transmits the detected data to the controller 140 (402).

Next, the learner 142 of the controller 140 learns the plurality of motions constituting the surgical task based on the motion data (e.g., F, x, v) acquired from the motion data detector 120 and the bio-data of the operator/patient acquired by one or more sensors or devices as discussed above (404).

The learner 142 stores the results of learning the plurality of motions constituting the surgical task, i.e. training data (motion data and bio-data of the operator and/or patient) and weighting values w in the case of supervised learning using ANNs, in the database 130a of the storage unit 130, and ends the learning procedure (406).

Figure 16:
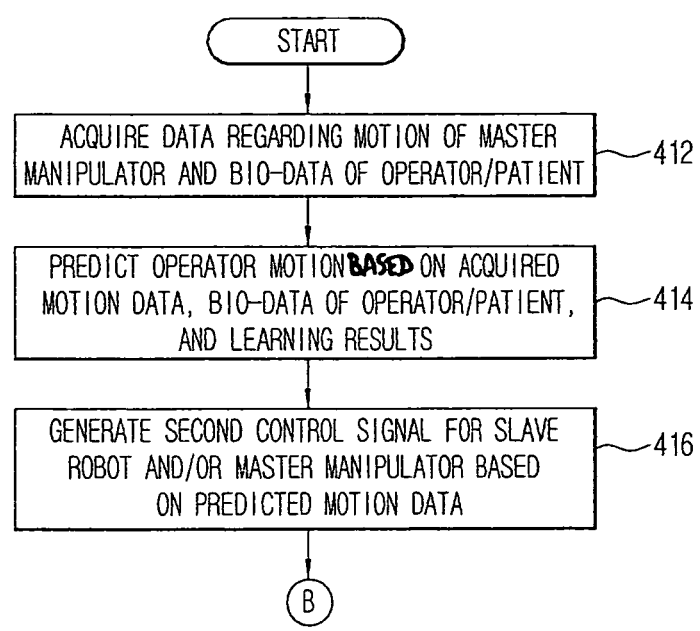
FIG. 16 is a flowchart illustrating a prediction procedure of the overall control algorithm of the surgical robot system.

FIG. 16 is a flowchart illustrating a prediction procedure of the overall control algorithm of the surgical robot system.

Explaining a prediction procedure of the overall control algorithm of the surgical robot system with reference to FIG. 16, first, the surgery is initiated and the operator of the master manipulator 112 (e.g., a doctor who uses the surgical robot system) performs a given surgical motion via the master manipulator 112.

When the operator of the master manipulator 112 performs the given surgical motion via the master manipulator 112, the motion data detector 120 detects data regarding the motion of the master manipulator 112. In addition, the bio-data detector 125 of the master robot 100 detects bio-data of the operator (e.g., the doctor) and the bio-data detector 220 of the slave robot 200 detects bio-data of the patient. The detected data regarding the motion of the master manipulator 112 and the detected bio-data of the operator and/or patient are transmitted to the controller 140 (412). Here, the data regarding the motion of the master manipulator 112 may include interactive force data F between the master manipulator 112 and the operator, position data x of the master manipulator 112, and speed data v of the master manipulator 112. In addition, the data may include various other data that may indicate the motion of the master manipulator 112 (e.g., acceleration data of the master manipulator 112). Also, the bio-data of the operator may include a heart rate for discrimination of the level of tension of the operator, and the bio-data of the patient may include an ECG, blood-pressure, breathing-rate, body-heat, and heart-rate information.

The predictor 143 included in the controller 140 predicts the operator motion based on the motion data (e.g., F, x, V) acquired from the motion data detector 120, the bio-data of the operator and/or patient acquired from the bio-data detectors 125 and 220, and the learning results illustrated in FIG. 15 (414). In this case, the predicted operator motion may include a plurality of motions constituting a surgical task, and a surgical task constituted by sequential connection of predicted basic motions.

The predictor 143 transmits the operator motion predicted as described above (e.g., the basic motion or the surgical task) to the second control signal generator 144 included in the controller 140.

Thereafter, the second control signal generator 144 generates a second control signal to control motions of the slave robot 200 and/or the master manipulator 112 (e.g., if the master manipulator has a redundant DOF) based on the operator motion predicted by the predictor 143 (e.g., the basic motion or the surgical task) (416).

Figure 17:
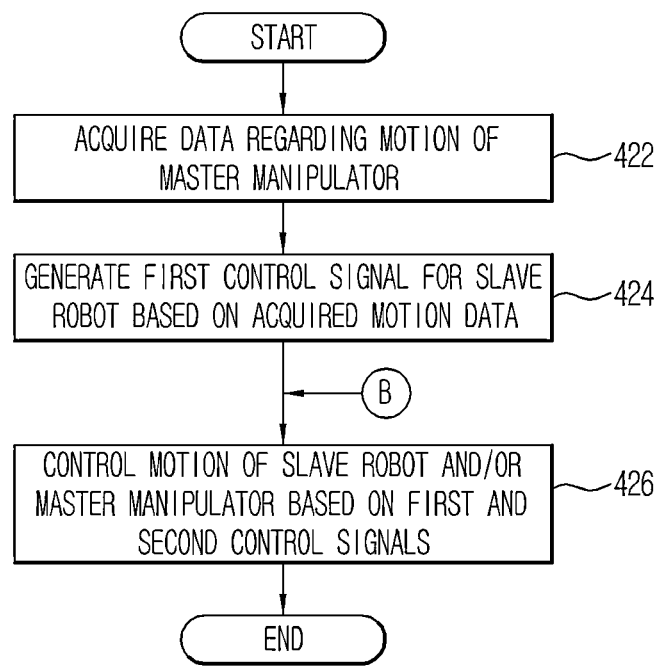
FIG. 17 is a flowchart illustrating a control method of the surgical robot system.

FIG. 17 is a flowchart illustrating a control method of the surgical robot system.

When the operator of the master manipulator 112 performs a given surgical motion via the master manipulator 112, the motion data detector 120 detects data regarding the motion of the master manipulator 112, and transmits the detected data regarding the motion of the master manipulator 112 to the controller 140 (422). Although FIGS. 16 and 17 are separately provided for differentiated description between the procedure of predicting the operator motion and the general control procedure of the surgical robot system, Operation 422 of FIG. 17 corresponds to Operation 412 of FIG. 16.

Next, the first control signal generator 141 included in the controller 140 generates a first control signal to control motions of the slave robot 200, i.e. motions of the main surgical tools 206, the auxiliary surgical tools 208, and/or the endoscope 210 based on the motion data (e.g., F, x, v) acquired from the motion data detector 120 (424).

The controller 140 controls motions of the slave robot 200 and/or the master manipulator 112 (e.g., if the master manipulator has a redundant DOF) based on the first control signal generated in Operation 424 and a second control signal generated in Operation 416 (326).

As is apparent from the above description, according to a surgical robot system and a control method thereof, an intelligent surgical robot system functions to predict an operator motion and to safely manipulate, e.g., a required auxiliary surgical tool during surgery based on the predicted motion, which may improve safety and accuracy of a surgical operation during a surgery.

Further, according to the surgical robot system and the control method thereof, as compared to a master manipulator of a conventional surgical robot system that functions as a simple joystick, it may be possible to allow an operator to perform surgery more comfortably and to move or fix all required surgical tools to or at an optimized surgical position.

While the disclosure herein has provided example embodiments of a surgical robot and control method to control the surgical robot, for example, in a medical setting to perform an operation on a patient (e.g., a human or animal or other life form), the disclosure is not so limited. For example, the disclosure may be directed to a robot used in other settings which may benefit from the surgical robot disclosed herein. For example, the robot may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the robot. The settings may include, for example, mining operations, surveillance operations, inspection operations, repair operations, bomb disposal operations, etc., however again, the disclosure is not so limited. Further, while the operator may be a doctor, the operator generally may be any user who uses the surgical robot or robot as disclosed herein, and need not be a doctor.

The apparatus and methods for controlling a configuration or operation mode of the surgical robot according to the above-described example embodiments may use one or more processors, which may include a microprocessor, central processing unit (CPU), digital signal processor (DSP), or application-specific integrated circuit (ASIC), as well as portions or combinations of these and other processing devices.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

Some example embodiments of the present disclosure can also be embodied as a computer readable medium including computer readable code/instruction to control at least one component of the above-described example embodiments. The medium may be any medium that can storage and/or transmission the computer readable code.

The computer readable code may be recorded in the medium, or may be transmitted via Internet. The medium, for example, may include read-only memory (ROM), random-access memory (RAM), compact disc (CD)-ROMs, magnetic tapes, floppy disks, optical data storage devices, and carrier waves such as data transmission through the Internet. The medium can also be a distributed over network coupled computer systems so that the computer readable code is stored and executed in a distributed fashion. In addition, examples of the component may include a processor or a computer processor. The element to be processed may be distributed and/or included in a single device. Some or all of the operations performed by the surgical robot according to the above-described example embodiments may be performed over a wired or wireless network, or a combination thereof.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Although the embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A control method of a robot system, the control method comprising:
   acquiring data regarding a motion of a master manipulator by an operator;
   reading, from a database, results of learning a plurality of motions constituting different ones of a plurality of tasks, the learning the plurality of motions being performed offline prior to the motion of the master manipulator by the operator;
   predicting which of the plurality of tasks is an executed task being performed by the operator and connecting the plurality of motions in a sequence associated with the executed task based on the acquired motion data and the results of learning the plurality of motions; and
   adjusting a tool so as to correspond to the executed task such that the tool is controlled based on the sequence associated with the executed task.

2. The control method according to claim 1, wherein the data regarding the motion of the master manipulator includes at least one of interactive force data between the master manipulator and the operator, position data of the master manipulator, and speed data of the master manipulator.

3. The control method according to claim 1, wherein the executed task includes one or more of suturing, passing, running, and cannulation.

4. The control method according to claim 1, wherein the plurality of motions associated with the executed task includes one or more of orient, push, and pull motions.

5. The control method according to claim 1, wherein the learning of the plurality of motions is performed via machine learning.

6. The control method according to claim 5, wherein the machine learning comprises:
   supervised learning in which the data regarding the motion of the master manipulator is acquired beforehand and is an input, and learning is performed in a state in which a target value for the input is known.

7. A robot system, comprising:
   a slave robot having a robot arm to which at least one tool is coupled; and
   a master robot to control the slave robot, the master robot including,
      a master manipulator configured to manipulate the robot arm;
      a motion data detector configured to detect data regarding a motion of the master manipulator by an operator; and
      a controller configured to,
         read, from a database, results of learning a plurality of motions constituting different ones of a plurality of tasks, the learning the plurality of motions being performed offline prior to the motion of the master manipulator by the operator,
         predict which of the plurality of tasks is an executed task being performed by the operator and connecting the plurality of motions in a sequence associated with the executed task based on the motion data detected via the motion data detector and the results of learning the plurality of motions constituting the executed task, and
         control the at least one tool so as to correspond to the executed task such that the tool is controlled based on the sequence associated with the executed task.

8. The system according to claim 7, wherein the motion data detector includes at least one of a force/torque sensor configured to detect interactive force data between the master manipulator and the operator, a position sensor configured to detect a position of the master manipulator, and a speed sensor configured to detect a speed of the master manipulator.

9. The system according to claim 7, wherein the task includes one or more of suturing, passing, running, and cannulation.

10. The system according to claim 7, wherein the plurality of motions constituting the task includes one or more of orient, push, and pull motions.

11. The system according to claim 7, wherein the controller includes:
    a first control signal generator configured to generate a first control signal to control a motion of the slave robot based on the data regarding the motion of the master manipulator acquired via the motion data detector;
    a learner configured to learn the plurality of motions constituting the task based on previously acquired data regarding the motion of the master manipulator;
    a predictor configured to predict the operator basic motion or the task based on the motion data detected via the motion data detector and the results of learning performed via the learner;
    a second control signal generator configured to generate a second control signal to control the motion of the slave robot and/or the master manipulator having a redundant degree of freedom (DOF) based on the predicted basic motion or task; and
    an image processor configured to process an image input from an endoscope coupled to the robot arm, and to output a picture image.

12. The system according to claim 7, further comprising:
    a storage configured to store, in the database, the results of learning the plurality of motions constituting the task acquired via the learner, and a reference image including at least one of an X-ray image, a Computed Tomography (CT) image, and a Magnetic Resonance Imaging (MRI) image.

13. The system according to claim 7, further comprising:
    a display unit configured to display an endoscopic image corresponding to an image signal provided from an endoscope coupled to the robot arm.

14. The control method according to claim 1, further comprising:
    selectively providing image data suitable for the predicted basic motion, or controlling zoom by changing a focal length of a zoom lens of a camera provided in an endoscope that is one kind of the tool.

* * * * *